(12) United States Patent
Al-Otaibi et al.

(10) Patent No.: US 9,052,146 B2
(45) Date of Patent: Jun. 9, 2015

(54) COMBINED COOLING OF LUBE/SEAL OIL AND SAMPLE COOLERS

(75) Inventors: Abdullah M. Al-Otaibi, Dhahran (SA); Montaser A. Al-Mubayidh, Dhahran (SA)

(73) Assignee: Saudi Arabian Oil Company (SA)

( * ) Notice: Subject to any disclaimer, the term of this patent is extended or adjusted under 35 U.S.C. 154(b) by 1196 days.

(21) Appl. No.: 12/960,888

(22) Filed: Dec. 6, 2010

(65) Prior Publication Data

US 2012/0138268 A1    Jun. 7, 2012

(51) Int. Cl.
| | |
|---|---|
| *G01N 33/00* | (2006.01) |
| *F28D 7/14* | (2006.01) |
| *F28D 7/00* | (2006.01) |
| *F28D 7/02* | (2006.01) |
| *F28D 7/10* | (2006.01) |
| *F28F 9/00* | (2006.01) |
| *G01N 1/22* | (2006.01) |
| *F28F 1/12* | (2006.01) |
| *F28F 1/42* | (2006.01) |
| *F28F 9/013* | (2006.01) |
| *F28F 9/02* | (2006.01) |

(52) U.S. Cl.
CPC ............... *F28D 7/14* (2013.01); *F28D 7/0066* (2013.01); *F28D 7/024* (2013.01); *F28D 7/028* (2013.01); *F28D 7/106* (2013.01); *F28F 1/124* (2013.01); *F28F 1/426* (2013.01); *F28F 9/001* (2013.01); *F28F 9/013* (2013.01); *F28F 9/026* (2013.01); *G01N 1/2247* (2013.01); *G01N 2001/2282* (2013.01)

(58) Field of Classification Search
CPC . F28D 15/043; F28D 15/0266; G10N 1/2247; G10N 2001/2282
USPC ............... 422/547, 559, 565, 146; 436/38; 165/104.14

See application file for complete search history.

(56) References Cited

U.S. PATENT DOCUMENTS

| | | | |
|---|---|---|---|
| 853,092 A | 5/1907 | Knoth | |
| 2,146,312 A * | 2/1939 | Powell et al. | 324/443 |

(Continued)

FOREIGN PATENT DOCUMENTS

| | | |
|---|---|---|
| CN | 2323343 | 6/1999 |
| CN | 101338958 | 1/2009 |

(Continued)

OTHER PUBLICATIONS

International Search Report issued in application No. PCT/US2011/063503, mailed on Aug. 23, 2012.

(Continued)

*Primary Examiner* — Jill Warden
*Assistant Examiner* — Dwayne K Handy
(74) *Attorney, Agent, or Firm* — Bracewell & Giuliani LLP; Constance Gall Rhebergen; Linda L. Morgan

(57) ABSTRACT

A heat exchanger that is useful for analyzing samples, such as condensate, and methods of cooling a sample for analysis are provided as embodiments of the present invention. The heat exchanger includes an inner tube for containing cooling water and an annulus for containing steam so that heat exchange occurs between the cooling water and the steam so that condensate forms in the annulus. An external shield is attached to the heat exchanger to provide additional natural cooling and to prevent users from contacting the steam contained within the annulus.

23 Claims, 12 Drawing Sheets

(56) References Cited

U.S. PATENT DOCUMENTS

| | | |
|---|---|---|
| 2,259,433 A | 10/1941 | Kitto |
| 3,651,551 A | 3/1972 | Cannon |
| 3,976,129 A | 8/1976 | Silver |
| 4,241,043 A | 12/1980 | Hetzel |
| 4,392,526 A | 7/1983 | Hage et al. |
| 4,585,059 A | 4/1986 | Lee |
| 4,661,459 A * | 4/1987 | Hirtz ............................. 436/25 |
| 5,046,548 A | 9/1991 | Tilly |
| 5,174,369 A | 12/1992 | Glass |
| 5,732,769 A | 3/1998 | Staffa |
| 5,832,738 A | 11/1998 | Shin |
| 6,098,704 A | 8/2000 | Tsuchiya et al. |
| 6,214,292 B1 * | 4/2001 | Las Navas Garcia ........... 422/63 |
| 6,427,717 B1 | 8/2002 | Kimura |
| 2002/0157815 A1 | 10/2002 | Sutter |
| 2003/0209345 A1 | 11/2003 | Zweig |
| 2007/0000652 A1 * | 1/2007 | Ayres ........................... 165/158 |
| 2009/0308051 A1 | 12/2009 | Henderson et al. |
| 2010/0170665 A1 | 7/2010 | Lovato |

FOREIGN PATENT DOCUMENTS

| | | |
|---|---|---|
| CN | 101738110 | 6/2010 |
| FR | 2494829 | 5/1982 |
| JP | 63180092 | 7/1988 |
| WO | 0222341 | 3/2002 |
| WO | 2003037799 | 8/2003 |
| WO | 2005024329 | 3/2005 |
| WO | 2006126700 | 11/2006 |

OTHER PUBLICATIONS

Rosemount Analytical Inc., "Hagan Sample Cooler Styles 374901-001 and 374901-002," Product Data Sheet, Model 503, PDS 106-901.A01, May 2006, www.raihome.com.

* cited by examiner

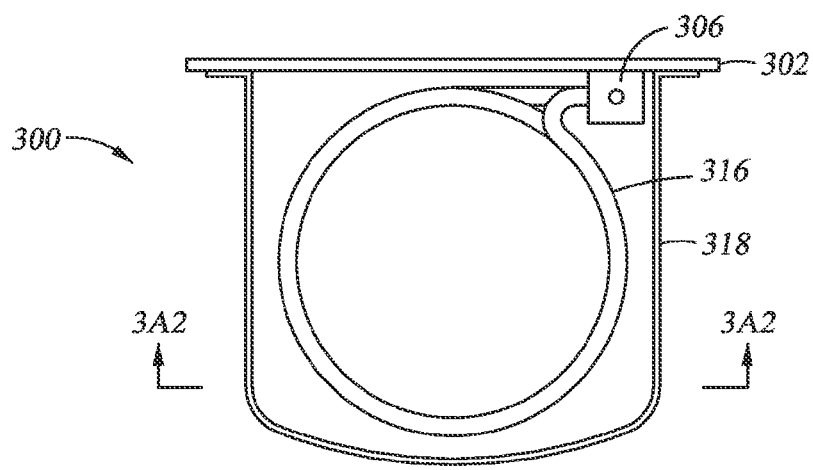
Fig. 3A1
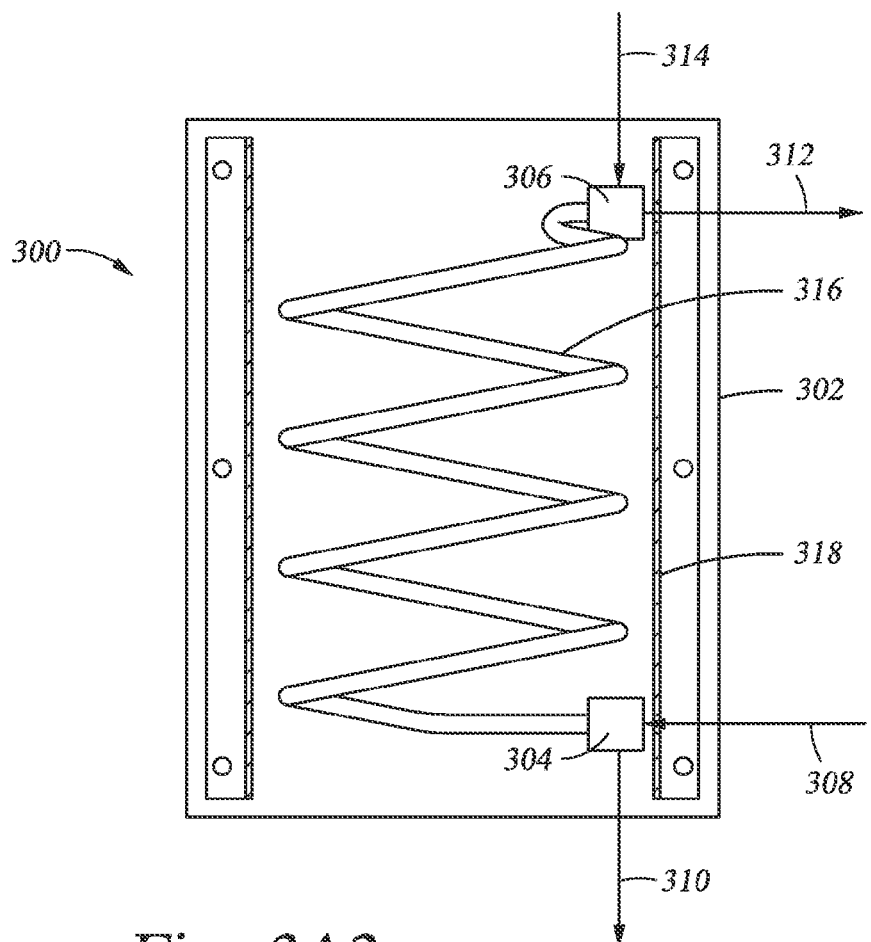
Fig. 3A2

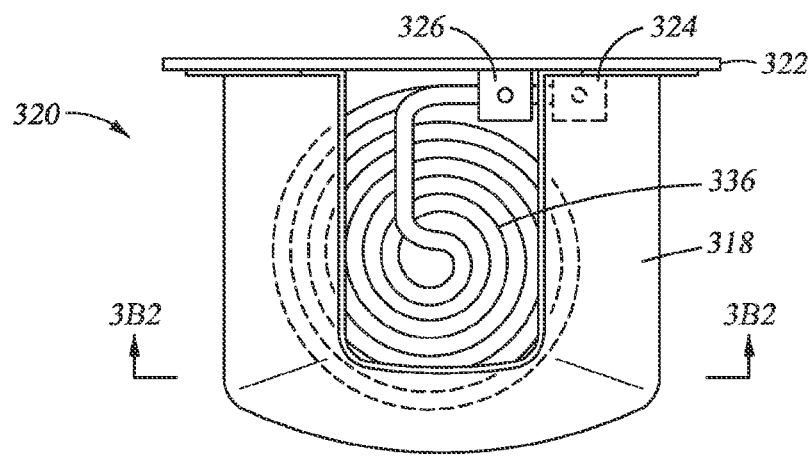
Fig. 3B1
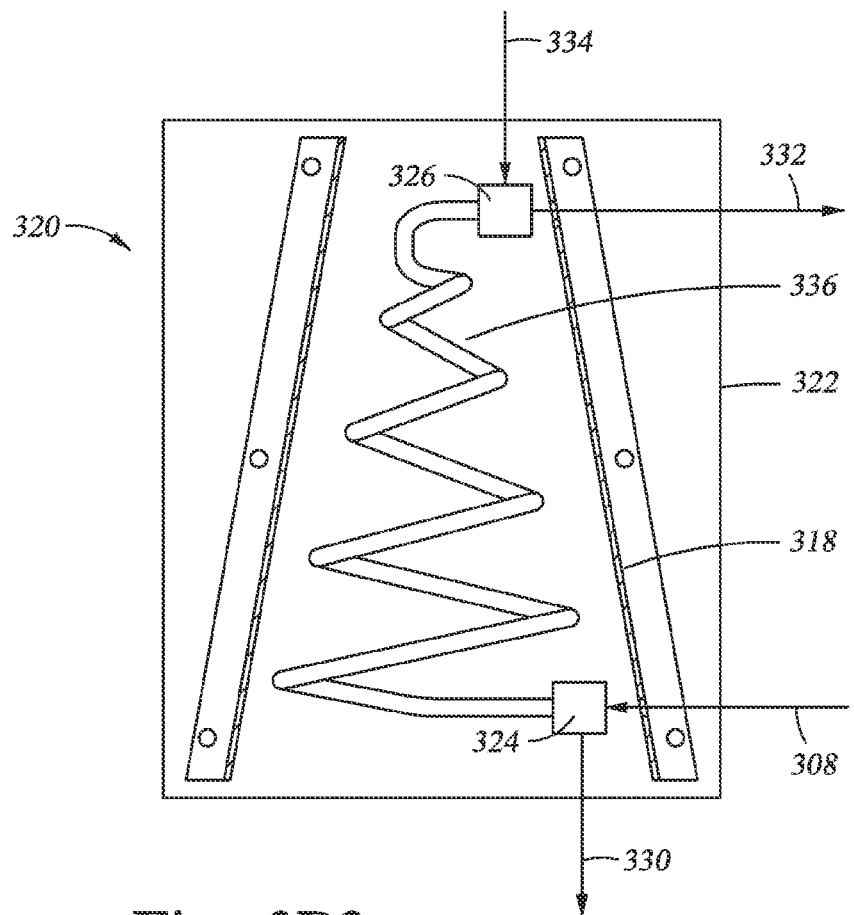
Fig. 3B2

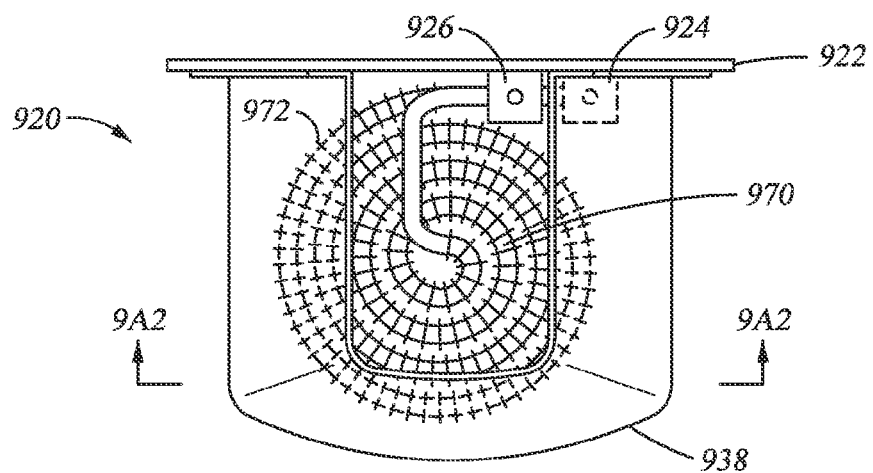
Fig. 9A1
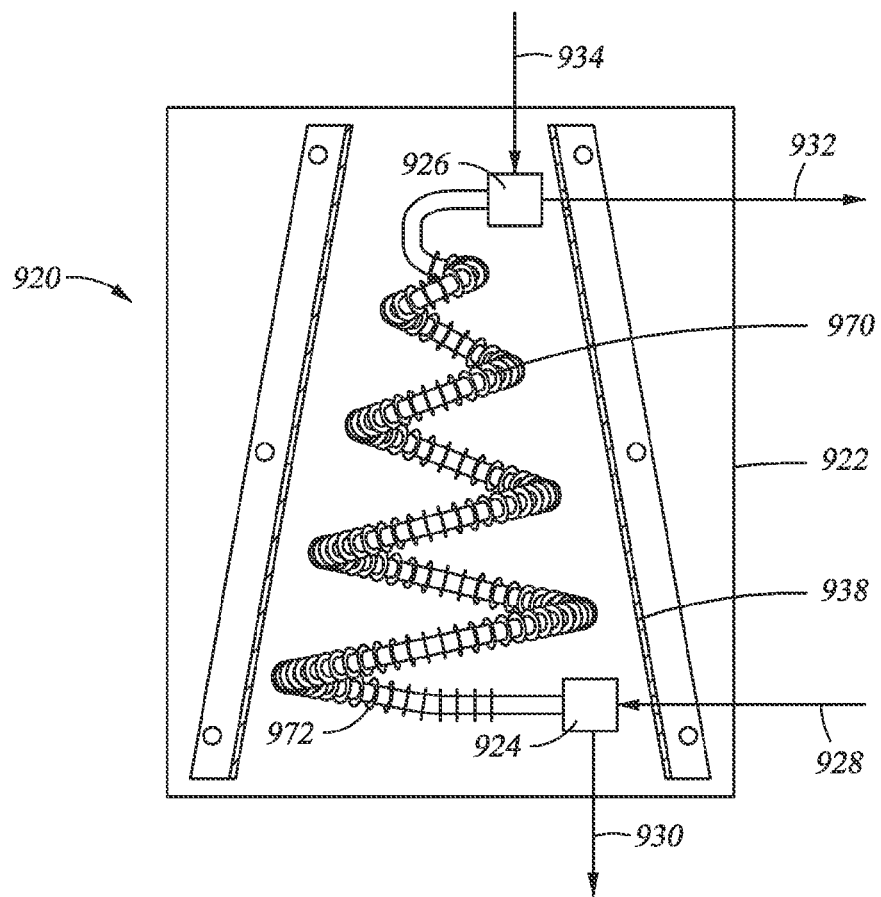
Fig. 9A2

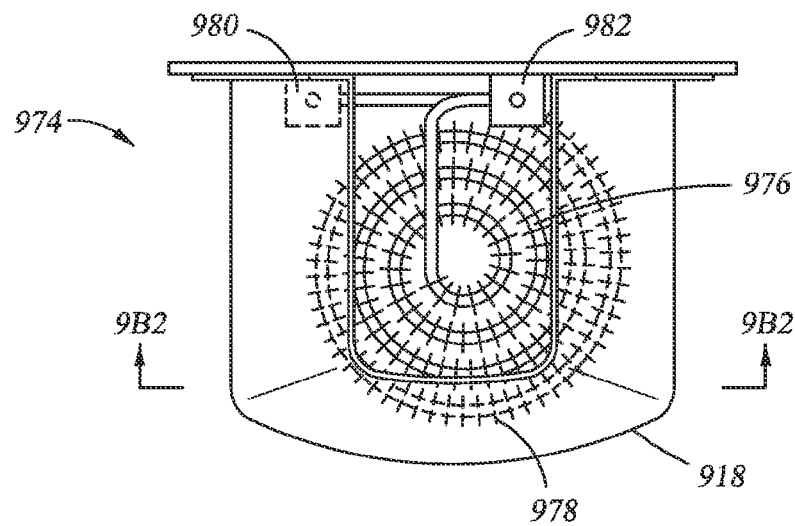
Fig. 9B1
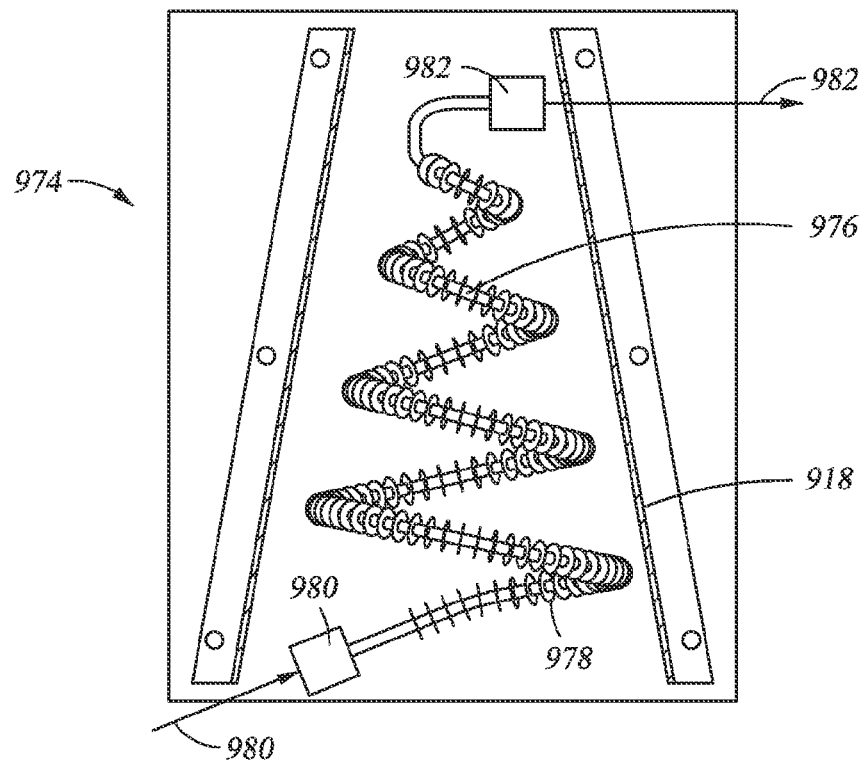
Fig. 9B2

COMBINED COOLING OF LUBE/SEAL OIL AND SAMPLE COOLERS

BACKGROUND OF THE INVENTION

1. Field of the Invention

The present invention relates to heat exchangers. More specifically, the present invention relates to heat exchangers useful for analyzing samples, such as condensate samples.

2. Description of the Related Art

Heat exchangers can have many uses in chemical plants and refineries. Most exchangers use at least two conduits in which a cooler stream and a warmer stream are used to force heat exchange between the two streams. Traditionally, the cooler stream is in the "outer" area of the exchanger, while the warmer stream is in the "inner" area of the exchanger. Many times the operating conditions of such heat exchangers can cause problems, such as pluggage or fouling due to precipitation of salts, which ultimately result in failure of a part of the heat exchanger. Other causes of pluggage or fouling can include the precipitation of salts in areas of the heat exchanger, such as in the annulus from the cooling water due to localized high temperature, and stagnant areas along the coil cooler due to its configuration of having inner tube to outer tube surface contact. Such pluggage or fouling can affect the quality of the streams contained within the heat exchangers. This is particularly problematic when the streams are required to be maintained within established specifications.

A need exists for configurations and methods of operating heat exchangers that minimize the possibility of failures due to pluggage in the piping. A need also exists for configurations and methods of operating heat exchangers that will reduce the potential for fouling in the streams contained within the heat exchangers. It would be advantageous if such configurations and methods of operating the heat exchangers were simple and relatively inexpensive to implement.

SUMMARY OF THE INVENTION

In view of the foregoing, a heat exchanger that is useful for analyzing samples, such as condensate, and methods of cooling a sample for analysis are provided as embodiments of the present invention. For example, as an embodiment, a heat exchanger for analyzing samples is provided. The heat exchanger includes an outer wall of the heat exchanger; an inner tube for containing cooling water; an annulus for containing steam so that heat exchange occurs between the cooling water and the steam so that condensate is formed in the annulus; and an external shield attached to the heat exchanger to prevent contact with the steam contained within the annulus of the heat exchanger. The external shield also allows air to provide additional cooling between the outer wall of the heat exchanger and the external shield. The inner tube forms a coil. The annulus is generally located between an outer surface of the inner tube and an inner surface of the outer wall of the heat exchanger.

Besides the heat exchanger embodiments, processes for cooling a sample are also provided as embodiments of the present invention, in this embodiment, cooling water flows through an inner tube of a heat exchanger and steam flows through an annulus of the heat exchanger so that heat exchange occurs between the cooling water and the steam so that condensate is produced in the annulus. Air is allowed to circulate between the annulus and an external shield to provide additional cooling to the steam contained in the annulus of the heat exchanger. The external shield is also operative to prevent users from contacting the steam contained within the annulus of the heat exchanger. The sample is then analyzed.

Besides use as a sample cooling system, the heat exchanger of the present invention can also be used as a seal and lube oil cooler for pumps and compressors, which also have many failures and improper cooling due the coolers fouling. Other suitable uses for the heat exchanger embodiments and related methods of the present invention will be apparent to those of skill in the art and are to be considered within the scope of the present invention.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

FIG. 3a1 is a top view schematic of a cooler system having a uniform coil made in accordance with embodiments of the present invention.

FIG. 3a2 is a front sectional schematic view of the cooler system of FIG. 3a1, taken along the 3A2-3A2 line.

FIG. 3b1 is a top view schematic of a cooler system having an inclined coil made in accordance with embodiments of the present invention.

FIG. 3b2 is a front sectional schematic view of the cooler system of FIG. 3b1, taken along the 3B2-3B2 line.

FIG. 9a1 is a top view schematic of a finned tube heat exchanger system having both air and water cooling made in accordance with embodiments of the present invention.

FIG. 9a2 is a front sectional schematic view of the cooler system of FIG. 9a1, taken along the 9A2-9A2 line.

FIG. 9b1 is a top view schematic of a finned tube heat exchanger system having air cooling made in accordance with embodiments of the present invention.

FIG. 9b2 is a front sectional schematic view of the cooler system of FIG. 9b1, taken along the 9B2-9B2 line.

DETAILED DESCRIPTION OF THE DISCLOSURE

Figure 1:
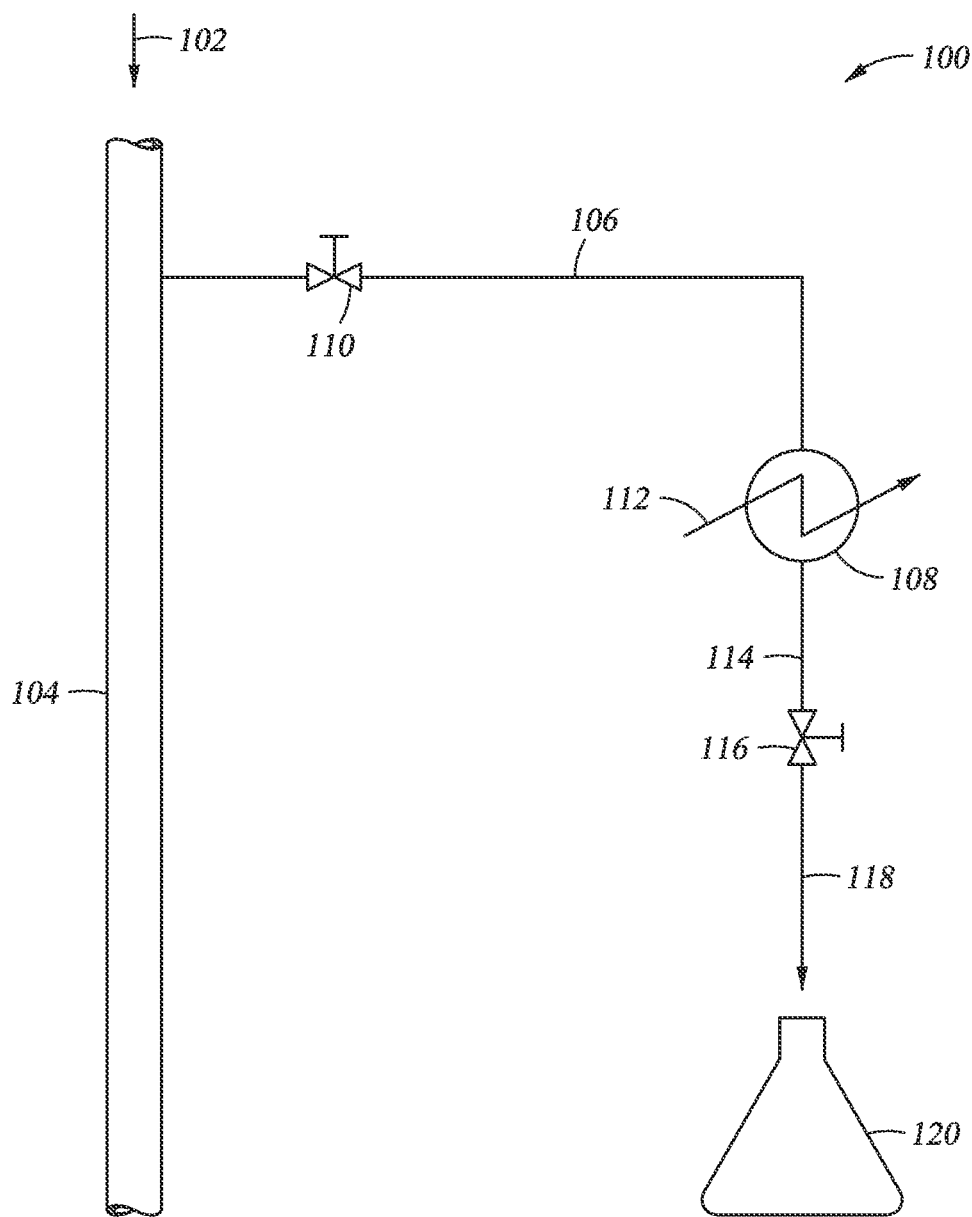
FIG. 1 is a schematic of a sample cooler system made in accordance with embodiments of the present invention.

A heat exchanger that is useful for analyzing condensate or other samples and methods of cooling a sample for analysis are provided as embodiments of the present invention. For example, as an embodiment, a heat exchanger for analyzing samples is provided, such as those shown in FIG. 1. The heat exchanger includes an outer wall of the heat exchanger; an inner tube for containing cooling water; an annulus for containing steam so that heat exchange occurs between the cooling water and the steam so that condensate is formed in the annulus; and an external shield attached to the heat exchanger to prevent contact with the steam contained within the annulus of the heat exchanger, as shown in FIGS. 3a and 3b. The external shield also allows air to provide additional cooling between the outer wall of the heat exchanger and the external shield. The inner tube forms a coil. The annulus is generally located between an outer surface of the inner tube and an inner surface of the outer wall of the heat exchanger. Embodiments of the present invention generally relate to helical double pipes or tubes.

Referring back to FIG. 1, heat exchanger system 100 can include process steam 102 flowing through process tubing 104. Steam can refer to any fluid which is to be cooled. Sample inlet 106 can be tubing leading from process tubing 104 to sample cooler 108. Isolating valve 110 can be used to control flow from process tubing 104 into sample cooler 108. Sample cooler 108 can be a heat exchanger used to cool a sample of process steam 102. Cooling water 112 can pass through sample cooler 108 to reduce the temperature of the sample of process steam 102. Tubing 114, which can be controlled by an optional control valve 116, can be used to control the transfer of the cooled sample 118 of process steam into a container such as sample bottle 120.

Figures 2, 2A:
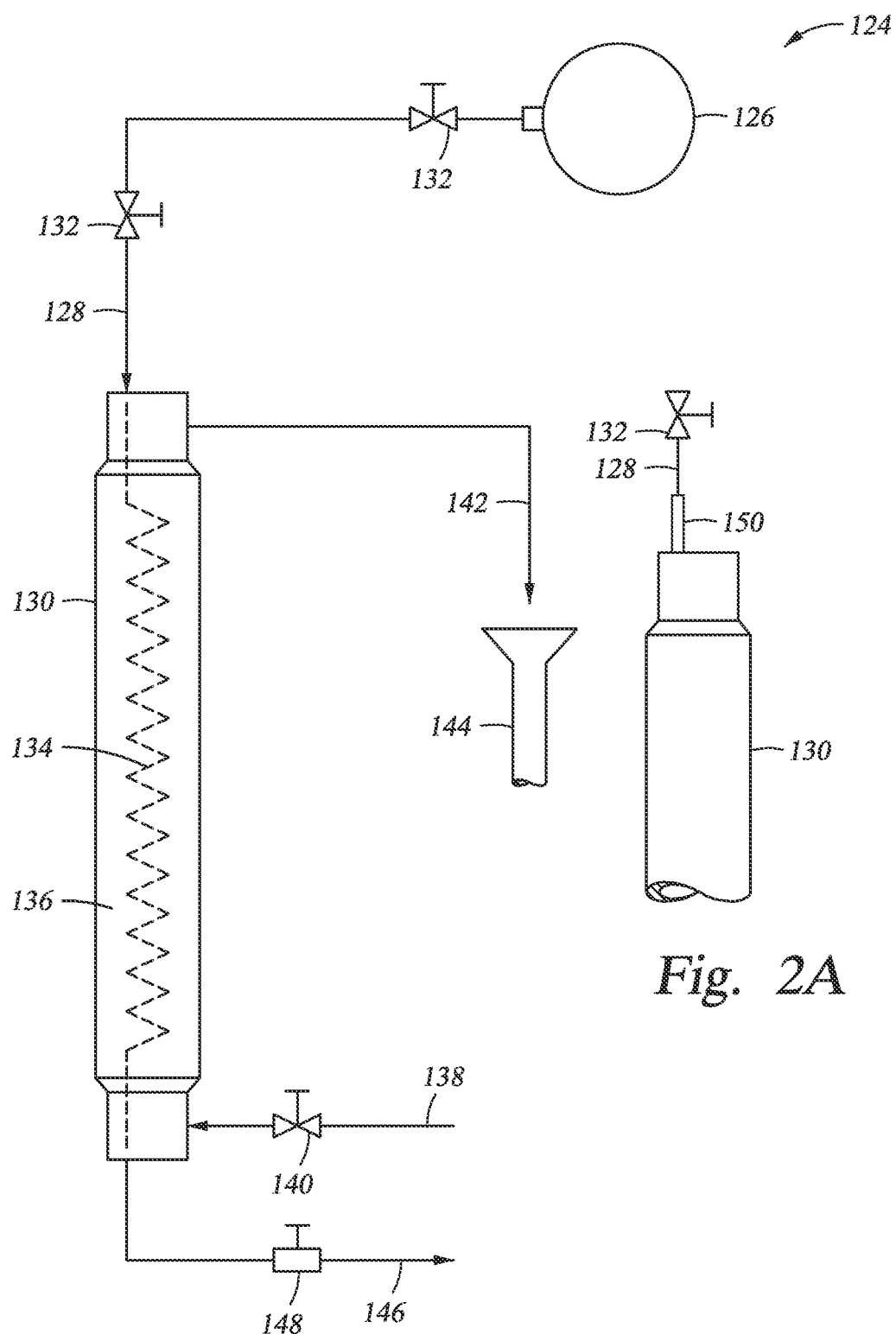
FIG. 2 is a schematic of a sample cooler system made in accordance with prior art embodiments.
FIG. 2a is a schematic of another embodiment of the sample cooler system made in accordance with prior art embodiments.

FIG. 2 shows a typical heat exchanger configuration where the steam is contained within the inner tube and the cooling water is contained within the annulus. By switching the flow and having the cooling water in the inner tube, the tube fouling issue is substantially reduced or all together avoided.

The external shield can be vertical, as shown in FIG. 3a, or inclined, as shown in FIG. 3b. Using the external shield around the coil can be used as personnel protection and assist in cooling down the steam naturally since more cooling will be available without having additional area.

Figure 4A:
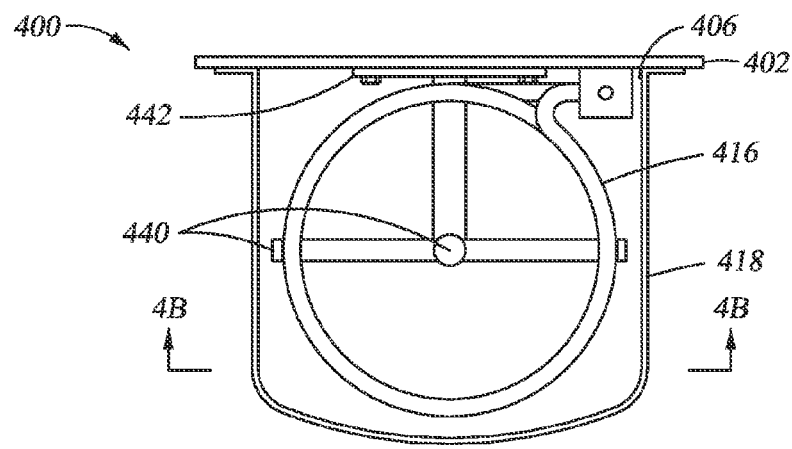
FIG. 4a is a top view schematic of a cooler system having a coil with longitudinal support made in accordance with embodiments of the present invention.
Figure 4B:
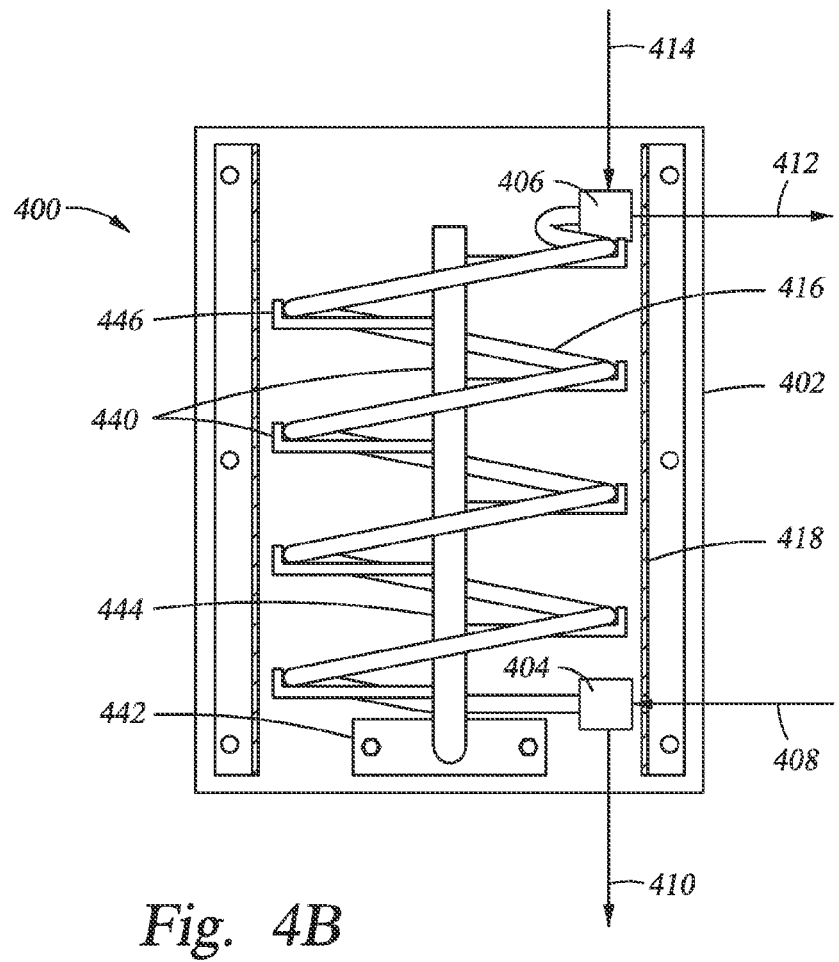
FIG. 4b is a front sectional schematic view of the cooler system of FIG. 4a, taken along the 4B-4B line.

Several configurations are available for the coil. The coil can include uniform circles, as shown in FIG. 3a, or inclined circles, as shown in FIG. 3b. The coil can be made of circles that are attached, or circles that are apart, such as those shown in FIG. 4, with or without support. In an aspect, the heat exchanger of the present invention further includes a longitudinal support for supporting the inner tube. Other suitable configurations for the coil will be apparent to those of skill in the art and are to be considered within the scope of the present invention.

As shown in FIG. 2, heat exchanger system 124 can include process tubing 126. Steam sample inlet 128 can be tubing leading from process tubing 126 to heat exchanger 130. One or more inlet control valves 132 can be located along steam sample inlet 128 to control the flow of steam from process tubing 126 to heat exchanger 130. Heat exchanger 130 can have an inner tube 134 that passes through annulus 136. Cooling water can be introduced into annulus 136 through cooling water inlet 138, which optionally can be controlled by inlet valve 140. The cooling water can pass through annulus 136 and out through cooling water outlet 142. In one embodiment, the cooling water can flow to drain 144. The process steam that flows into heat exchanger 130 can pass through inner tube 134 and out through sample outlet 146, which can be controlled by valve 148. As shown in FIG. 2A, sample inlet 128 can be, in certain embodiments, connected to heat exchanger 130 by socket weld connection 150.

Referring back to FIGS. 3a1 and 3a2, in one embodiment, heat exchanger 300 can include mounting plate 302. Connection blocks 304 and 306 can be attached to mounting plate 302. Connection block 304 can include chilled or otherwise temperature controlled ("tempered") water inlet 308 and steam outlet 310. Connection block 306 can include tempered water outlet 312 and steam inlet 314. The inlets 308, 314 and outlets 310, 312 can each be in communication with passages through cooler, or coil, 316. The tempered water can flow through an inner tube within coil 316. The steam, which can be any gas or liquid fluid to be cooled, can flow through the annulus between the exterior of the inner tube and the outer wall of coil 316. In certain embodiments, the circles, or turns, of coil 316 can be approximately the same diameter such that the coil has a cylindrical shape from bottom to top. Personal protection plate 318 can be a shield around coil 316 that can function as a personal protection plate to reduce the chances of a person contacting coil 316.

Referring back to FIGS. 3b1 and 3b2, in one embodiment, heat exchanger 320 can include mounting plate 322. Connection blocks 324 and 326 can be attached to mounting plate 322. Connection block 324 can include tempered water inlet 308 and steam outlet 330. Connection block 326 can include tempered water outlet 332 and steam inlet 334. The inlets and outlets can each be in communication with passages through cooler, or coil, 336. The tempered water can flow through an inner tube within coil 336. The steam can flow through the annulus between the exterior of the inner tube and the outer wall of coil 336. In certain embodiments, each turn of the coil can have a smaller diameter than the previous turn, such that the coil has a tapered shape from bottom to top. Personal protection plate 318 can be a shield around coil 336 that can function as a personal protection plate to reduce the chances of a person contacting coil 336.

Referring back to FIGS. 4a and 4b, in one embodiment, heat exchanger 400 can include mounting plate 402. Connection blocks 404 and 406 can be attached to mounting plate 402. Connection block 404 can include tempered water inlet 408 and steam outlet 410. Connection block 406 can include tempered water outlet 412 and steam inlet 414. The inlets and outlets can each be in communication with passages through cooler, or coil, 416. The tempered water can flow through an inner tube within coil 416. The steam can flow through the annulus between the exterior of the inner tube and the outer wall of coil 416. In certain embodiments, the turns of coil 416 can be approximately the same diameter such that the coil has a cylindrical shape from bottom to top. Personal protection plate 418 can be a shield around coil 416 that can function as a personal protection plate to reduce the chances of a person contacting coil 416. Coil support 440 can be used to support coil 416. Coil support 440 can include coil support base 442, which can be mounted to mounting plate 402. Coil support stem 444 can be connected to coil support base 442, and support arms 446 can extend from coil support stem 444. Support arms 446 can support a portion of various turns of coil 416.

Besides the heat exchanger embodiments, processes for cooling a sample are also provided as embodiments of the present invention. In this embodiment, cooling water flows through an inner tube of a heat exchanger and steam flows through an annulus of the heat exchanger so that heat exchange occurs between the cooling water and the steam so that condensate is produced in the annulus. Air is allowed to circulate between the annulus and an external shield to provide additional cooling to the steam contained in the annulus of the heat exchanger. The external shield is also operative to prevent users from contacting the steam contained within the annulus of the heat exchanger. The sample, such as condensate, is then analyzed. Embodiments of the present invention can be used to ensure product quality and/or equipment integrity.

Figure 5A:
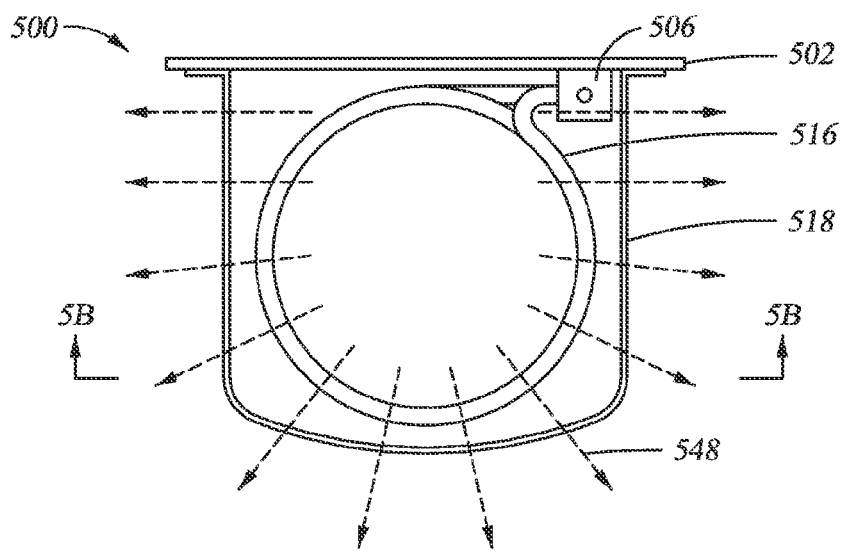
FIG. 5a is a top view schematic of a cooler system having natural air circulation around the coil made in accordance with embodiments of the present invention.
Figure 5B:
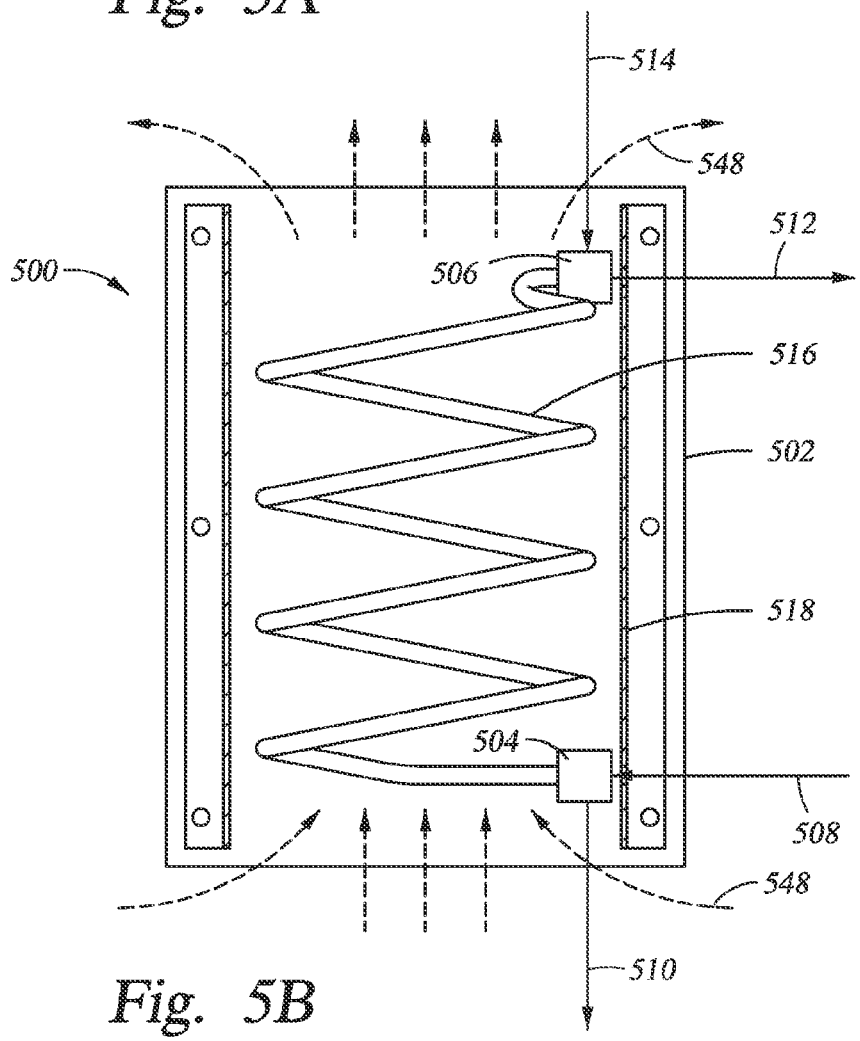
FIG. 5b is a front sectional schematic view of the cooler system of FIG. 4a, taken along the 5B-5B line.

Referring back to FIGS. 5a and 5b, in one embodiment, heat exchanger 500 can have air circulation 548 flowing through an open bottom and open top of personal protection plate 518 such that the air circulation 548 flows across the exterior surface of coil 516. Heat exchanger 500 can include mounting plate 502. Connection blocks 504 and 506 can be attached to mounting plate 502. Connection block 504 can include tempered water inlet 508 and steam outlet 510. Connection block 506 can include tempered water outlet 512 and steam inlet 514. The inlets and outlets can each be in communication with passages through cooler, or coil, 516. The tempered water can flow through an inner tube within coil 516. The steam can flow through the annulus between the exterior of the inner tube and the outer wall of coil 516. In general, the circles, or turns, of coil 516 can be approximately the same diameter such that the coil has a cylindrical shape from bottom to top. Personal protection plate 518 can be a shield around coil 516 that can function as a personal protection plate to reduce the chances of a person contacting coil 516.

Figure 6:
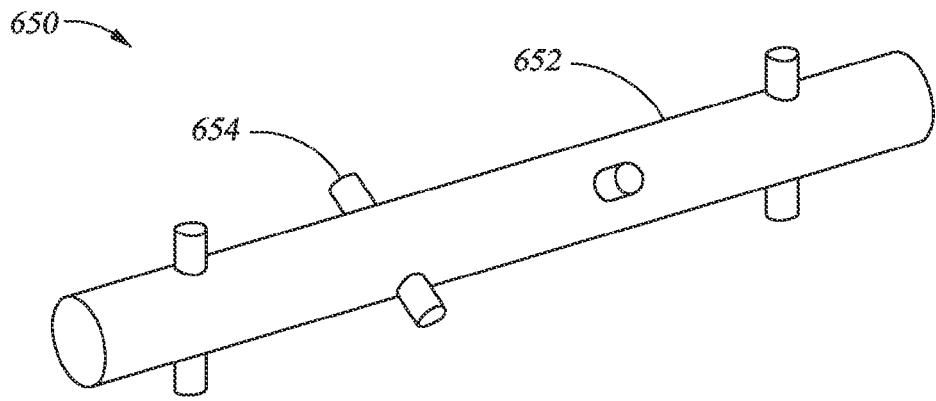
FIG. 6 is a schematic of an inner tube having external studs for use in a heat exchanger made in accordance with embodiments of the present invention.

Various features can be used with the inner and outer tubes. For example, in an aspect, the inner tube includes a studded tube. When the studded tube is used, flow directed plates can be used in embodiments of the present invention, as shown in FIG. 6. The studs maintain a distance between the two tubes by maintaining certain gab all around the inner tube to avoid any dead areas. Moreover, the studs can increase flow turbulence and heat transfer efficiency as well as the plates that can be oriented helically to enhance the heat transfer. As another example, the outer tube includes a dimpled tube. The outer tube can also have external indentations. The studs and the dimples can maintain a distance between the two tubes by maintaining certain gap all around the inner tube to avoid any dead areas and have more flow that is turbulent. The arrangement of the dimples is controlled to provide more turbulent flow and better heat transfer when compared with randomly placed dimples. Other suitable features that can be used in embodiments of the present invention will be apparent to those of skill in the art and are to be considered within the scope of the present invention.

Still referring to FIG. 6, studded tube 650 can include inner-tube 652 and a plurality of external studs 654. Inner-tube 650 can be the tube through which the cooling water flows. The process steam can flow on the exterior of inner tube 650, within an annulus defined by the exterior of inner tube 650 and an outer tube (not shown in FIG. 6). External studs 654 can be any type of spacer affixed or integral to inner-tube 652. External studs 654 can be any length up to about the maximum gap distance of the annulus. External studs 654 can help to keep inner tube 652 centered within the outer tube and thus promote flow all around inner tube 652.

Additional sources of cooling can be used in embodiments of the present invention. For example, the heat exchanger of the present invention can also include an external wind fan. In an aspect, natural air can be circulated around the coil, as shown in FIG. 5 to aid it cooling the steam. The protective shield helps when there is an external wind fan to provide natural cooling to the steam to cool down the steam and reduce the coil surface area, as per FIG. 5. The air inside the protective shield is heated by the coil and becomes lighter. The heated air is pushed by the cold air so that continuous air circulation that cools the coil externally is provided. Forced cooling can be also implemented as shown in FIG. 11. When forced cooling is used, a wind fan or solar source can be used to drive the fan above the cooler. The cooler also can be at the top or bottom of the exchanger. The forced cooling can be used alone or with other cooling mechanisms.

Besides being used to analyze condensate, embodiments of the present invention can be used in applications that require cooling down or heating streams for different applications. For example, some of the other applications in which the heat exchangers of the present invention can be used include sample cooling, analyzer pre-cooling, seal coolers, condensers, cryogenic vaporizers, compressor inter-coolers, compressor after-coolers, general applications, and the like. Other applications in which the heat exchanges of the present invention can be used will be apparent to those of skill in the art and are to be considered within the scope of the present invention.

In embodiments of the present invention, the cooler can include a combination of any of the disclosed features. For example, the coil can be uniform, inclined, in contact or apart circles, with or without support. The potential combinations are based on many factors; such as weight and cooling dominant. The features that will be advantageous for a particular application will be apparent to those of skill in the art and will be considered within the scope of the present invention.

It may require replacing the inner tube with a tube that is externally studded with or without flow directed plates, as shown in FIG. 6. The studs maintain a distance between the two tubes by maintaining certain gap all around the inner tube to avoid any dead areas. Moreover, the studs can increase flow turbulence and heat transfer efficiency as well as the plates that is oriented helically for more enhancement to the heat transfer.

Figure 7A:
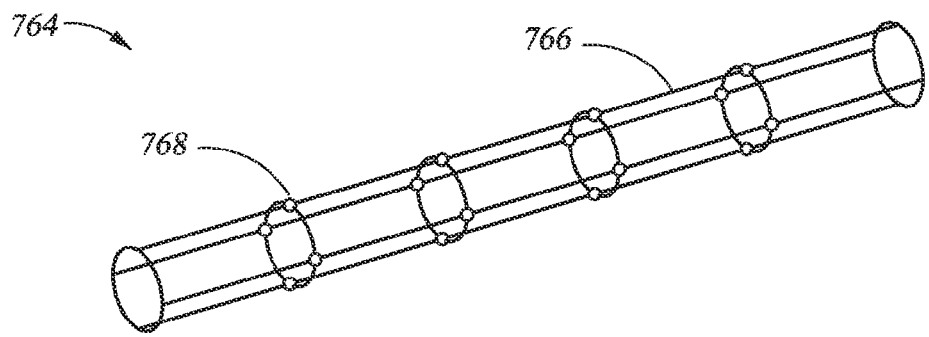
FIG. 7a is a schematic of wiring mesh support for use in a heat exchanger made in accordance with embodiments of the present invention.
Figure 7B:
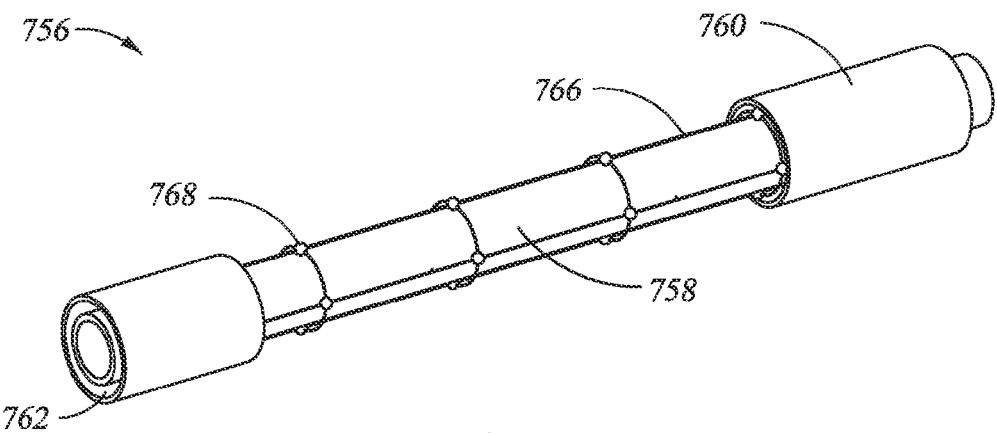
FIG. 7b is a schematic of mesh support in the annulus for use in a heat exchanger made in accordance with embodiments of the present invention.

In an aspect, the heat exchanger can also include a wiring mesh with support balls, as shown in FIG. 7a, which can be installed in the annulus between the two tubes and fixed at the piping connection boxes at both ends on the coil, as shown in FIG. 7b, which can also be used to maintain the annulus gap and create turbulent flow.

Referring to FIG. 7b, tubing 756 can have inner pipe, or inner tube, 758 and outer pipe, or outer tube, 760 (outer tube 760 is shown partially cut away to reveal inner tube 758). Cooling water can flow through inner tube 758 while process steam can flow through annulus 762, defined by the outer diameter of inner tube 758 and the inner diameter of outer tube 760. Referring to FIGS. 7a and 7b, spacer mesh 764 can be located on the outer diameter of inner tube 758. Spacer mesh 764 can include a mesh support 766, which can be a web of metallic or non-metallic strands of connection wires that extend axially, circumferentially, or both axially and circumferentially around inner tube 758. Spacers such as support balls 768 can be attached to or integral with mesh support 766 at various locations. Support balls 768 can have a greater diameter than mesh support 766. When spacer mesh 764 is installed in tubing 756, support balls 768 can maintain a predetermined gap between the outer diameter of inner tube 758 and the inner diameter of outer tube 760. Mesh support 766 can maintain the proper location and spacing of support balls 768 during installation and operation of tubing 756. The proper spacing can help keep inner tube 758 relatively centered within outer tube 760, thus permitting process steam to flow on all sides of the outer diameter of inner tube 758.

Figure 8A:
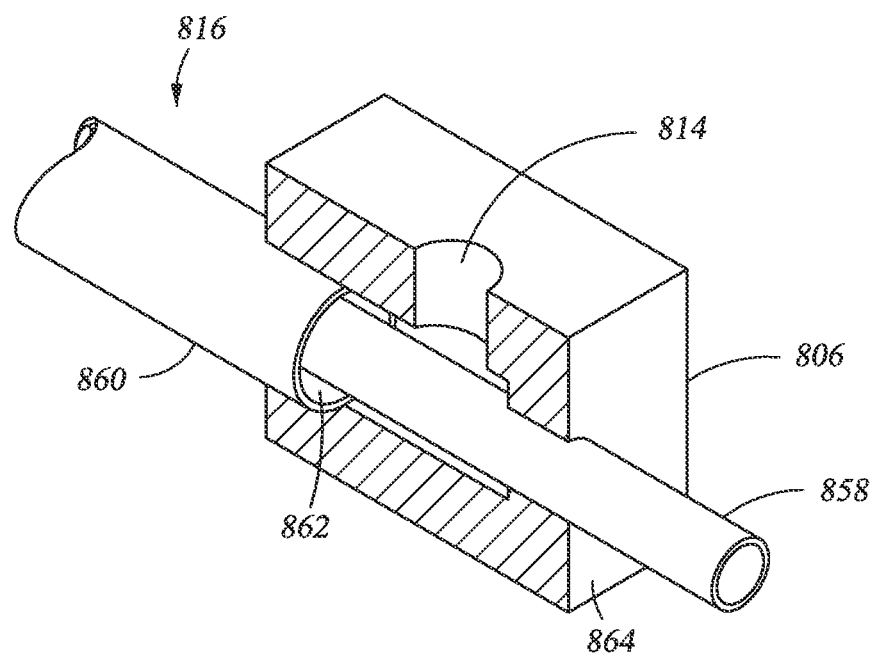
FIG. 8a is a schematic of a steam-side inlet for use in a heat exchanger made in accordance with embodiments of the present invention.
Figure 8B:
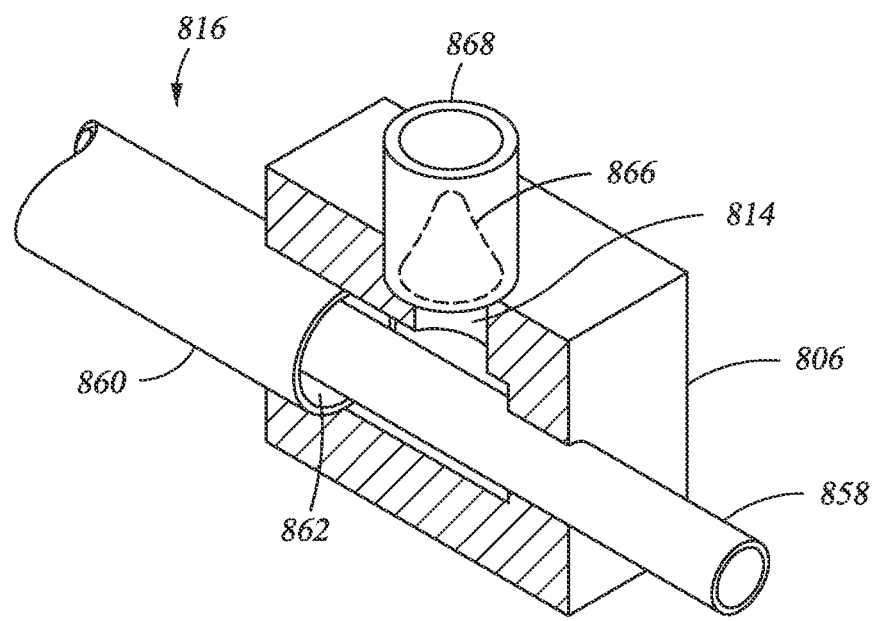
FIG. 8b is a schematic of a complete assembly of a nipple and flow distributor for use in a heat exchanger made in accordance with embodiments of the present invention.

Various features can be added to the heat exchanger to protect the inner tube from an external erosion issue. For example, as shown in FIG. 8a, the steam inlet connection can be modified. As another example, as shown in FIG. 8b, a distributor cone can be installed inside a nipple connected to the tubes connection box to protect the inner tube from an external erosion issue that may develop because of the steam entering to the heat exchanger. Using the steam inlet distributor can extend the tube life by protecting it from expected external erosion.

Referring to FIGS. 8a and 8b, tube connection box 806 can be used to connect inlet and outlet lines to tubing coil 816. Tubing coil 816 can include inner tube 858, which can pass through outer tube 860. Annulus 862 can be the gap between the outer diameter of inner tube 868 and the inner diameter of outer tube 860. Tube connection box 806 can be used to communicate a fluid, such as process steam, into or out of annulus 862. In the embodiments shown in FIGS. 8a and 8b, steam-side inlet 814 can be a connection point that is in communication with the interior of tube connection box 806. Tube connection boxes can be used as an inlet connection box 806 or an outlet connection box 804. Outer tube 860 can connect to tube connection box 806 while inner tube 858 can pass through tube connection box 806 and terminate at or beyond the sidewall 864. The interior of tube connection box 806, thus, is in communication with annulus 862 but the interior of inner tube 858 is not in communication with the interior of tube connection box 806.

In the embodiment shown in FIG. 8b, a flow distributor 866 can be located within nipple 868 of the steam-side inlet 814 or can be located within tube connection box 806. Flow distributor 866 can deflect the flow of process steam so that it is not flowing directly onto the outer diameter of inner tube 858 as it passes through tube connection box 806. Flow distributor 866 can be any shape including, for example, a cone shape.

In addition to the above modification, fins can be used to enhance the external cooling for the steam using the circulated air, as shown in FIG. 9a, to have both air and water cooling. Air cooling alone may be enough to cool down the steam to the required temperature based on the steam temperature and flow rates, as shown in FIG. 9b. For high steam temperature, the combined cooling can be utilized. The steam is cooled first by air in a separate cooler to avoid high calcium carbonate ($CaCO_3$) precipitation rate, then enters the second cooler where it cooled down to the required temperature using both air/water as shown in FIG. 10.

Referring back to FIGS. 9a1 and 9a2, heat exchanger 920 can include fins to increase surface area and improve heat transfer from the process steam. In the embodiment shown, coil 970 can be a coil having an inner tube, an outer tube, and an annulus therebetween (not shown in FIG. 9a). Fins 972 can be located on the exterior of coil 970 to increase surface area and improve heat transfer between coil 970 and the air, or other fluid, in contact with the exterior of coil 970. Heat exchanger 920 can include mounting plate 922. Connection blocks 924 and 926 can be attached to mounting plate 922. Connection block 924 can include tempered water inlet 928 and steam outlet 930. Connection block 926 can include tempered water outlet 932 and steam inlet 934. The inlets and outlets can each be in communication with passages through coil, 970. The tempered water can flow through an inner tube within coil 970. The steam can flow through the annulus between the exterior of the inner tube and the outer wall of coil 970. In general, each turn of the coil can have a smaller diameter than the previous turn, such that the coil has a tapered shape from bottom to top. Air can flow between personal protection plate 938 to facilitate heat transfer from coils 970 and fins 972.

Referring to FIGS. 9B1 and 9B2, heat exchanger 974 can use air cooling, alone, to cool process steam. Coil 976 can be a length of tubing having only one passage therethrough. Fins 978 can be located on the exterior of coil 976. Process steam can enter coil 976 at steam inlet 980, pass through coil 976, and exit through steam outlet 982. Air can flow through personal protection plate 918 and transfer heat from process steam, through coil 976, to the air. Fins 978 can increase the rate of heat transfer from process steam to the air.

Figure 10:
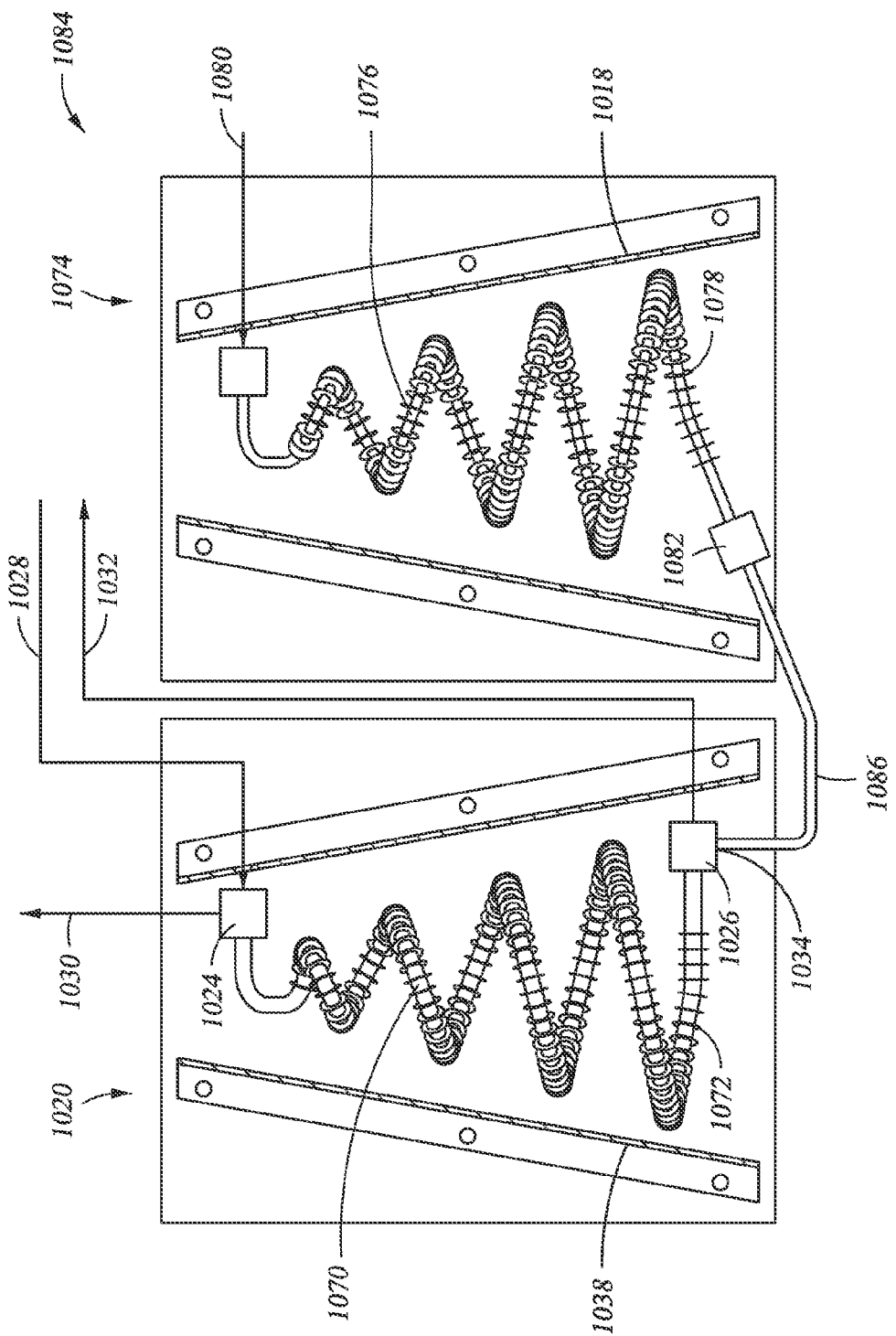
FIG. 10 is a schematic of a two-stage heat exchanger system using air and water cooling in the first stage and only air in the second stage made in accordance with embodiments of the present invention.

Referring to FIG. 10, heat exchanger 1084 can include heat exchanger 1074 and heat exchanger 1020 connected in series. Heat exchanger 1074 can be an air heat exchanger that can initially cool process steam. The partially cooled process steam can then flow through steam connection tubing 1086 into heat exchanger 1020, which can be a water cooling or combined air/water cooling heat exchanger. In the embodiment shown, process steam can enter steam inlet 1080 and flow through external finned steam coil cooler 1076 to steam outlet 1082. Fins 1078 can be located on external finned steam coil cooler 1076. Steam outlet 1082 can be connected to steam connection 1086, which can transfer the partially-cooled steam to steam inlet 1034 on connection block 1026. The steam can be further cooled as it passes through the annulus of external finned water/steam coil cooler 1070, which can have fins 1072. The now cooled process steam can then pass through steam outlet 1030 at connection block 1024. Cooling water can flow through water inlet 1028 of connection block 1024 and into the inner tube (not shown in FIG. 10) of external finned water/steam cooler 1070, where it can cool the process steam. The water can flow out through water outlet 1032 of connection block 1026. One or more personal protection plates 1018, 1038 can be used to shield the coils and to guide air flow around the coils. The entire assemblies can be mounted on one or more mounting plates 1022 and 1018.

Figure 11A:
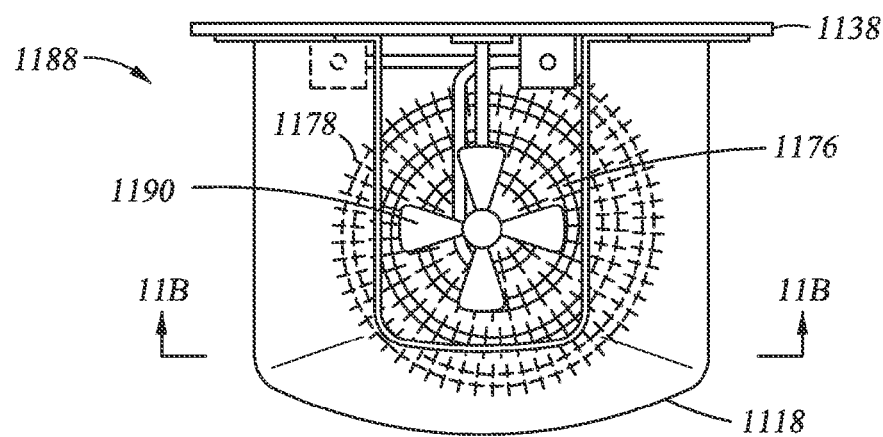
FIG. 11a is a top view schematic of a heat exchanger system having forced cooling using a wind fan made in accordance with embodiments of the present invention.
Figure 11B:
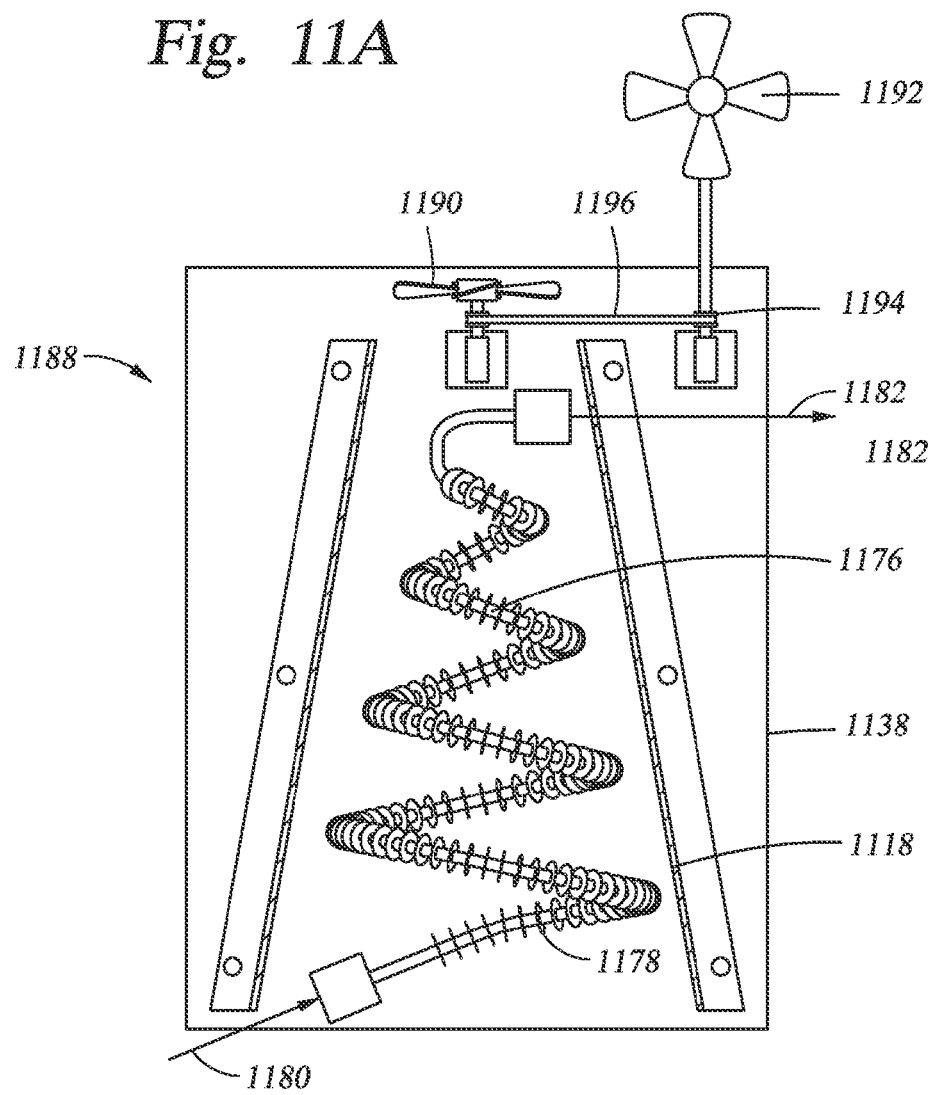
FIG. 11b is a front sectional schematic view of the cooler system of FIG. 11a, taken along the 11A-11A line.

Referring to FIG. 11a and 11b, heat exchanger 1188 can use a device to promote air flow across external finned steam coil cooler 1176. Heat exchanger 1188 can include mounting plate 1138, upon which other components can be mounted. Coil 1176 can be a length of tubing having only one passage therethrough, or can be a different type of heat exchanger tubing such as tubing having an outer tube and an inner tube and an annulus therebetween. Fins 1178 can be located on the exterior of coil 1176. Process steam can enter coil 1176 at steam inlet 1180, pass through coil 1176, and exit through steam outlet 1182. Air can flow through personal protection plate 1118 and transfer heat from the process steam, through coil 1176, to the air. An air handler, such as fan 1190 can be used to increase the flow of air through personal protection plate 1118 and, thus, across external finned steam coil cooler 1176. Air handler 1190 can be connected to mounting plate 1138. In one embodiment, fan 1190 can be powered by a non-electric source such as, for example, wind fan 1192, which can be connected to fan 1190 by gear 1194 and belt 1196. Wind, such as naturally occurring wind, can cause wind fan 1192 to rotate. That rotation can be transferred by gear 1194 and belt 1196 to fan 1190. As fan 1190 rotates, it can pull or push air across external finned steam coil cooler. Other configurations can be used to transfer force from wind fan 1192 to fan 1190. Other configurations of fans can be used such as, for example, placing the fan below coil 1176.

In typical heat exchangers, cooling water is often times supplied to the annulus, while steam is supplied to the inner tube. By reversing the flow streams, fouling can be mitigated by having the cooling water in the inner pipe. By supplying cooling water to the inner pipe, the inner pipe is not easily fouled, can be cleaned easily, and can be replaced if required.

As an advantage of the present invention, a cost savings can be realized because the heat exchangers will not fail as often as they did with the traditional configuration and methods of operation. Not only will a cost savings be realized, but embodiments of the present invention will also have a positive safety impact because of the decreased heat exchanger failure rate. Furthermore, smooth operation of the heat exchanger assists in monitoring process and product reliability and keeps the operators who collect samples safer compared with the traditional configuration and methods of operation.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

What is claimed is:

1. A heat exchanger for analyzing samples, the heat exchanger comprising:
   a. an outer wall of the heat exchanger, the outer wall forming a coil;
   b. an inner tube for containing cooling water, the inner tube forming a coil that is circumscribed by the outer wall and that has a cooling water inlet and cooling water outlet so that the inner tube is in fluid communication with a cooling water system;
   c. an annulus for containing steam so that heat exchange occurs between the cooling water and the steam so that condensate is formed in the annulus; the annulus being located between an outer surface of the inner tube and an inner surface of the outer wall of the heat exchanger, the annulus having a steam inlet and steam outlet so that the annulus is in fluid communication with the steam system; and
   d. an external shield attached to the heat exchanger to prevent contact with the steam contained within the annulus of the heat exchanger and to allow air to provide additional cooling between the outer wall of the heat exchanger and the external shield.

2. The heat exchanger of claim 1 further comprising a longitudinal support for supporting the inner tube.

3. The heat exchanger of claim 1, wherein the inner tube comprises a studded tube.

4. The heat exchanger of claim 1, wherein the outer wall comprises a dimpled tube.

5. The heat exchanger of claim 1, further comprising a support meshing in the annulus between the inner tube and the outer wall.

6. The heat exchanger of claim 1, further comprising a steam-side inlet.

7. The heat exchanger of claim 1, further comprising a nipple and a flow distributor.

8. The heat exchanger of claim 1, wherein the outer wall comprises a finned tube to enhance external cooling.

9. The heat exchanger of claim 1, further comprising an external wind fan.

10. The heat exchanger of claim 1, wherein the coil is inclined.

11. The heat exchanger of claim 1, further comprising a second inner tube connected to the first inner tube to provide a second stage for cooling.

12. A process for cooling a sample of steam comprising the steps of:
   a. flowing cooling water through an inner tube of a heat exchanger, the inner tube forming a coil;
   b. flowing the sample of steam through an annulus of the heat exchanger so that heat exchange occurs between the cooling water and the steam so that a sample condensate is produced, the annulus being located between an outer surface of the inner tube and an inner surface of an outer wall of the heat exchanger, the outer wall of the heat exchanger forming a coil that circumscribes the inner tube;
   c. allowing air to circulate between the annulus and an external shield attached to the heat exchanger, the external shield being operative to prevent users from contacting the sample of steam contained within the annulus of the heat exchanger; and
   d. transferring the sample condensate into a container for analyzing the sample condensate.

13. The process of claim 12 further comprising a longitudinal support for supporting the inner tube.

14. The process of claim 12, wherein the inner tube comprises a studded tube.

15. The process of claim 12, wherein the outer comprises a dimpled tube.

16. The process of claim 12, further comprising a support meshing in the annulus between the inner tube and the outer wall.

17. The process of claim 12, further comprising a steam-side inlet.

18. The process of claim 12, further comprising a nipple and a flow distributor.

19. The heat exchanger of claim 12, wherein the outer wall comprises a finned tube to enhance external cooling.

20. The process of claim 12, further comprising an external wind fan.

21. The process of claim 12, further comprising an external protective shield to prevent contact with the steam contained within the annulus of the heat exchanger.

22. The process of claim 12, wherein the coil is inclined.

23. The process of claim 12, further comprising supplying the cooling water to a second inner tube connected to the first inner tube to provide a second stage for cooling the sample of steam.

* * * * *

UNITED STATES PATENT AND TRADEMARK OFFICE
CERTIFICATE OF CORRECTION

PATENT NO. : 9,052,146 B2
APPLICATION NO. : 12/960888
DATED : June 9, 2015
INVENTOR(S) : Abdullah M. Al-Otaibi et al.

Page 1 of 1

It is certified that error appears in the above-identified patent and that said Letters Patent is hereby corrected as shown below:

IN THE CLAIMS

In Column 10, Line 53, Claim 13, the second number appears as "12" and should read --12,--.

In Column 10, Line 57, Claim 15, the last three words appear as "outer comprises a" and should read --outer wall comprises a--.

Signed and Sealed this
Sixth Day of October, 2015

Michelle K. Lee
*Director of the United States Patent and Trademark Office*